United States Patent
Nguyen

(10) Patent No.: US 10,117,832 B2
(45) Date of Patent: Nov. 6, 2018

(54) EMULSIFIED FATTY ACIDS

(71) Applicant: BARLEAN'S ORGANIC OILS, LLC, Ferndale, WA (US)

(72) Inventor: Peter Nguyen, Renton, WA (US)

(73) Assignee: BARLEAN'S ORGANIC OILS, LLC, Ferndale, WA (US)

( * ) Notice: Subject to any disclaimer, the term of this patent is extended or adjusted under 35 U.S.C. 154(b) by 0 days.

(21) Appl. No.: 15/847,736

(22) Filed: Dec. 19, 2017

(65) Prior Publication Data
US 2018/0169011 A1 Jun. 21, 2018

Related U.S. Application Data

(60) Provisional application No. 62/436,634, filed on Dec. 20, 2016, provisional application No. 62/572,275, filed on Oct. 13, 2017.

(51) Int. Cl.
| | | |
|---|---|---|
| *A61K 8/67* | (2006.01) | |
| *A61K 9/107* | (2006.01) | |
| *A61K 47/22* | (2006.01) | |
| *A61K 47/26* | (2006.01) | |
| *A61K 47/10* | (2017.01) | |
| *A61K 31/201* | (2006.01) | |
| *A61K 31/202* | (2006.01) | |
| *A61K 47/34* | (2017.01) | |
| *A61K 47/46* | (2006.01) | |
| *A61K 47/12* | (2006.01) | |

(52) U.S. Cl.
CPC ............. *A61K 9/107* (2013.01); *A61K 8/678* (2013.01); *A61K 31/201* (2013.01); *A61K 31/202* (2013.01); *A61K 47/10* (2013.01); *A61K 47/12* (2013.01); *A61K 47/22* (2013.01); *A61K 47/26* (2013.01); *A61K 47/34* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 6,284,268 B1 | 9/2001 | Mishra et al. | |
| 8,741,373 B2 | 6/2014 | Bromley et al. | |
| 9,351,517 B2 | 5/2016 | Bromley | |
| 2006/0067922 A1* | 3/2006 | Christensen | A61K 9/0056 424/93.45 |
| 2008/0234376 A1 | 9/2008 | Lin et al. | |
| 2012/0016026 A1* | 1/2012 | Bromley | A23D 7/0053 514/560 |
| 2013/0017295 A1 | 1/2013 | Bromley | |
| 2013/0309362 A1* | 11/2013 | Bromley | A23L 2/52 426/72 |
| 2016/0345618 A1 | 12/2016 | Berl | |

FOREIGN PATENT DOCUMENTS

WO 2016/005230 1/2016

OTHER PUBLICATIONS

International Search Report and Written Opinion dated Mar. 1, 2018 in PCT/US2017/067425 (12 pages).
Emulsion Formation and Stability, First Edition. Edited by Tharwat F. Tadros. © 2013 Wiley-VCH Verlag GmbH & Co. KGaA. Published 2013 by Wiley-VCH Verlag GmbH & Co. KGaA. (76 pages).
Ese and Kilpatrick, "Stabilization of Water-in-Oil Emulsions by Naphthenic Acids and Their Salts: Model compounds, Role of pH, and Soap : Acid Ratio", Journal of Dispersion Science and Technology, vol. 25, No. 3, pp. 253-261, 2004 (10 pages).

* cited by examiner

*Primary Examiner* — Abigail Vanhorn
(74) *Attorney, Agent, or Firm* — FisherBroyles, LLP; Jason M. Pass

(57) ABSTRACT

Provided herein are methods and processes for emulsifying non-polar compounds, such as omega fatty acids. Also provided are compositions that can be prepared according to the methods and processes described herein. The compositions, for example, have a high amount of the non-polar compound, such as a large amount of omega fatty acids. The non-polar compounds are also present in very small droplets within composition. For example, the mean or median particle size of the droplets is less than about 5 μm. Further, the composition includes a low amount of surfactant, such as less than about 10-15% of the surfactant.

25 Claims, 6 Drawing Sheets

EMULSIFIED FATTY ACIDS

CROSS-REFERENCE TO RELATED APPLICATIONS

This application claims priority to U.S. provisional patent application Ser. No. 62/572,275, filed Oct. 13, 2017, and titled "Emulsified Fatty Acids," and to U.S. provisional patent application Ser. No. 62/436,634, filed Dec. 20, 2016, also titled "Emulsified Fatty Acids." The entire disclosures of the above-identified priority applications are hereby fully incorporated herein by reference.

TECHNICAL FIELD

The present invention relates generally to methods for emulsifying fatty acids, and more particularly to methods of making emulsified fatty acid compositions having a high percentage of fatty acid, the fatty acids being present in droplets with a reduced particle size.

BACKGROUND

Consumption of omega fatty acids are associated with numerous health benefits. A diet rich in omega-3 fatty acids, for example, is associated with lowered elevated blood triglyceride levels and hence a reduced risk of heart disease. An omega-3-rich diet is also associated with an improved blood glucose, a reduced risk of obesity, improved cognitive function, among several other benefits. As for omega-7 fatty acids, it has been suggested that this fatty acid can reduce high cholesterol and triglyceride levels, thus improving cardiovascular health. Consumption of omega-7 fatty acids has also been implicated in lowering insulin levels, improving liver function, and promoting weight loss. Omega-5 fatty acids have been shown to act a potent anti-oxidant, and are also believed to have anti-inflammatory properties. Omega-6 fatty acids have been implicated in playing an important role in brain function, and normal growth and development. Omega-6 fatty acids may also maintain bone health, regulate metabolism, and maintain a healthy reproductive system.

While the benefits of omega fatty acids are well recognized, providing readily-absorbable fatty acid products has proven challenging. This is due largely to the fact that non-polar compounds, such as fatty acids, are not easily dissolved in polar solutions such as water. Conventional emulsification processes, for example, often result in the coalescence of fatty acids into large droplets that are associated with poor bioavailability following consumption. Further, to reduce particle size of the droplets, large amounts of surfactants and/or solubilizing agents are often needed, thus increasing production costs and reducing the proportion of fatty acids that are ultimately present in the finished product. Surfactants and co-surfactants, for example, also have undesirable side-effects, and hence their use is disadvantageous or prohibitive in many applications. And even with the use of large amounts of surfactants and/or solubilizing agents, the particle sizes of the fatty acid droplets often remain larger than desired in the finished product, thus impacting bioavailability of the fatty acids when consumed.

Hence, what is needed is a cost-effective emulsification process that results in a final product having a high level of fatty acids. In addition to a high level of fatty acids, what is needed is a composition in which the emulsified droplets of the fatty acids have a small size, thus improving absorption when the emulsion is consumed. Also needed are emulsification processes that result in a small fatty-acid droplet size but yet do not rely on large amounts of solubilizing agents and/or surfactants.

SUMMARY

In certain example aspects, provided is a method for providing an emulsion. The method includes providing a first mixture, the first mixture including less than about 15% by weight of d-α-tocopheryl polyethylene glycol 1000 succinate ("TPGS") or derivative thereof. The mixture also includes a non-polar compound or mixture of non-polar compounds. The method also includes providing a second mixture, the second mixture including water and one or more emulsifiers. The one or more emulsifiers are, for example, less than about 15% of the second mixture. The method further includes combining the first mixture with the second mixture under high shear to form an emulsion of the non-polar compound or mixture of non-polar compounds. The non-polar compounds or mixture thereof are present, for example, in droplets having a particle size of about 5 μm or less and the non-polar compounds or mixture thereof comprise at least about 20% by weight of the emulsification.

In certain other example aspects, provided is a process for forming an emulsion. A lipid component is combined with an aqueous component (aqueous phase) under high shear mixing. The lipid component includes less than about 15% by weight of TPGS or derivatives thereof, and at least one or more non-polar compounds, such as an omega fatty acid. The aqueous component includes less that about 15% by weight of one or more emulsifiers, with the balance of the aqueous component being one or more carriers. The emulsion resulting from the combination of the lipid component and the aqueous component under high shear mixing includes at least about 20% by weight of the one or more non-polar compounds. Further, the emulsion includes droplets of the lipid component, the droplets having a particle size less than or equal to about 5 μm.

In certain example aspects, the non-polar compounds or mixture thereof are at least about 30% by weight of the emulsification and the TPGS is less than about 5% by weight of the emulsification. In certain example aspects, the non-polar compound or mixture thereof includes a fatty acid, such as an omega fatty acid. For example, the omega fatty acid can be an omega-3 fatty acid, an omega-5 fatty acid, an omega-6 fatty acid, an omega-7 fatty acid, or a mixture thereof.

In certain other example aspects, provided is an emulsion composition, such as an emulsion composition made according to the methods and processes for forming an emulsion described herein. The emulsion, for example, includes at least about 20% by weight of the one or more non-polar compounds, such at least about 20% by weight of omega fatty acids. The composition also includes less than about 15% by weight of the TPGS. The composition further includes droplets of the non-polar compounds having a particle size less than or equal to 5 μm.

In certain example aspects, the emulsion can further include a weak acid, such as citric acid, ascorbic acid, malic acid, or a combination thereof. In certain example aspects, the emulsion further comprises about 1-20% by weight glycerine. In certain example aspects, the emulsion further comprises xylitol, erythritol, or a combination thereof. In certain example aspects, the emulsion further comprises 1-5% by weight tocopherol and rosemary extract. In certain example aspects, the emulsion further comprises a preservative such as sorbic acid, potassium sorbate, sodium benzoate, or combination thereof.

In certain example aspects, provided is an emulsified lipid composition. The composition includes an emulsifier that is less than about 10% by weight of the composition. The composition also includes a surfactant that is less than about 10% by weight of the composition. The composition also includes one or more lipid compounds, the one or more lipids being at least about 20% by weight of the composition. Further, the one or more lipid compounds are present in emulsified droplets, the emulsified droplets having a particle size of about 5 µm or less.

These illustrative features are mentioned not to limit or define the disclosure, but to provide examples to aid understanding thereof. Additional embodiments are discussed in the Detailed Description, and further description is provided there.

DETAILED DESCRIPTION OF THE EXAMPLE EMBODIMENTS

Figure 1:
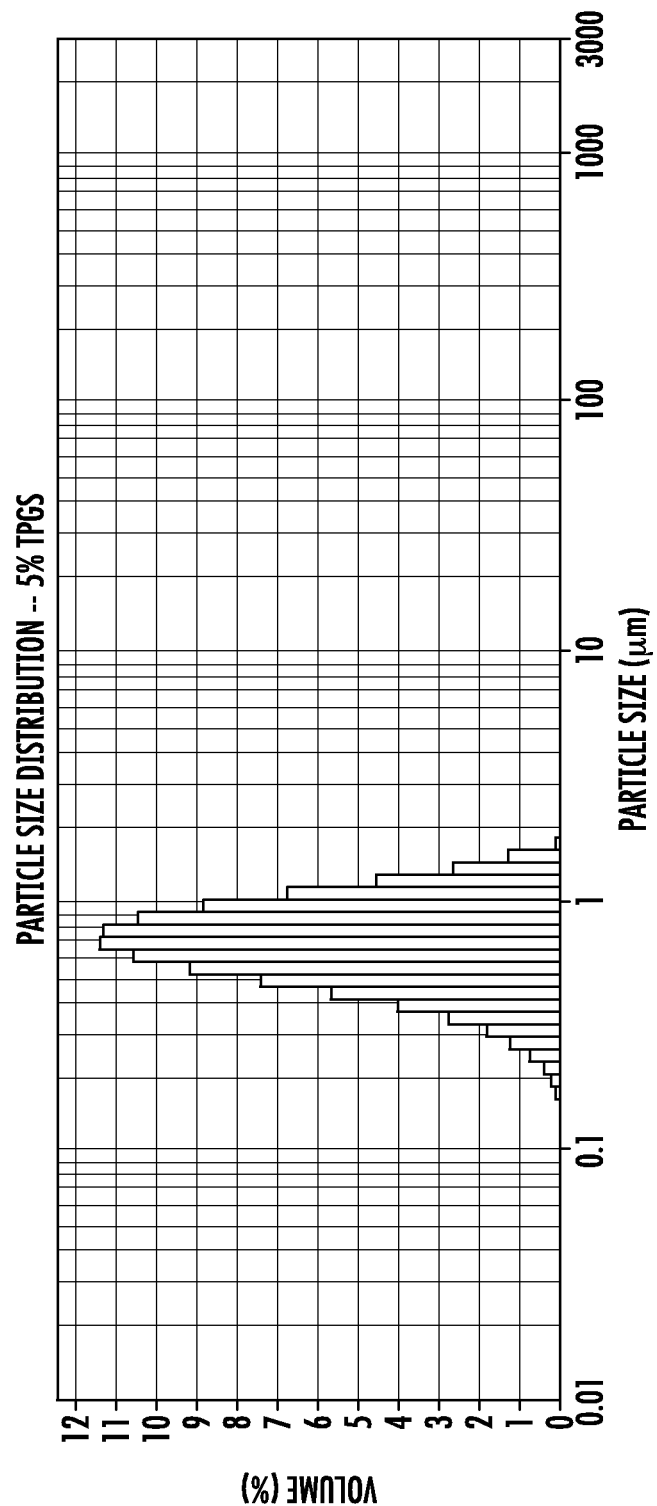
FIG. 1 is graph showing a differential histogram of particle size distribution for a sample in which 14.7% TPGS was used in the premix, in accordance with certain example embodiments. The resultant final product contained 29% non-polar component (oil) and 5% TPGS. The mean non-polar (oil) component particle size was 0.713 µm for the final product.

The embodiments described herein can be understood more readily by reference to the following detailed description, examples, and claims, and their previous and following description. Before the present system, devices, compositions and/or methods are disclosed and described, it is to be understood that the embodiments described herein are not limited to the specific systems, devices, and/or compositions methods disclosed unless otherwise specified, as such can, of course, vary. It is also to be understood that the terminology used herein is for the purpose of describing particular aspects only and is not intended to be limiting.

Further, the following description is provided as an enabling teaching of the various embodiments in their best, currently known aspect. Those skilled in the relevant art will recognize that many changes can be made to the aspects described, while still obtaining the beneficial results of this disclosure. It will also be apparent that some of the desired benefits of the present invention can be obtained by selecting some of the features of the various embodiments without utilizing other features. Accordingly, those who work in the art will recognize that many modifications and adaptations to the various embodiments described herein are possible and can even be desirable in certain circumstances and are a part of the present disclosure. Thus, the following description is provided as illustrative of the principles of the embodiments described herein and not in limitation thereof.

Overview

As described herein, provided are methods and processes for emulsifying non-polar compounds, such as omega fatty acids. Also provided are compositions that can be prepared according to the methods and processes describe herein. The compositions, for example, have a high amount of the non-polar compound, such as a large amount of omega fatty acids. The non-polar compounds are also present in very small droplets within composition. Further, the composition includes a low amount of surfactant.

More particularly, in certain examples the methods and process involve preparing a first mixture, the first mixture being a lipid component. The lipid component includes, for example, a large amount of non-polar compound or a mixture of non-polar compounds, such as a large amount of one or more fatty acids. In certain examples, the fatty acids are omega fatty acids. The lipid component also includes a low amount of a surfactant. In certain examples, the surfactant is d-α-tocopheryl polyethylene glycol 1000 succinate (TPGS) or a derivative thereof. TPGS is a tasteless and odorless, water-soluble form of Vitamin E, which the Food & Drug Administration has approved as vitamin E nutritional supplement. TPGS is also functions as an emulsion stabilizer.

Upon mixing the TPGS or derivate thereof with the non-polar compounds, a liquid premix is formed as a lipid component. While a co-surfactant may be added to the lipid component, the first mixture can be free or essentially free of any co-surfactant, as such co-surfactants ultimately reduce the total proportion of non-polar compounds. For example, such co-surfactants reduce the proportion of fatty acids that can be present in the final emulsified product.

In addition to the first mixture, a second mixture is prepared, the second mixture being an aqueous component. The aqueous component includes, for example, an emulsifier or mixture of emulsifiers or emulsion stabilizers that are mixed with a carrier. The carrier, for example, can be water or any other polar solution that is suitable for consumption. In certain examples, water can be mixed with another polar compound to form the carrier. Further, a variety of emulsifiers may be used, including a modified starch or gum mixtures such as gum arabic, xanthan gum, guar gum, modified gum acacia, and/or an ester gum.

Once the aqueous component (second mixture) is formed, the lipid component (first mixture) is slowly added to the aqueous component under high shear mixing conditions. The lipid component is slowly added until the desired amount of lipid component has been mixed with the aqueous component. The high shear mixing, for example, homogenizes the two components into an oil-in-water-type emulsion, with the "oil" portion being the non-polar compounds, such as omega fatty acids.

In certain examples, various other additives and components may be added to the emulsion. For example, other components may be added during preparation of the aqueous component and/or during the mixing of the lipid phase with the aqueous phase. Such components include, for example, flavorings, sweeteners, colorings, preservatives, stabilizers, humectants, pH adjusters, antioxidants, and/or other additives.

The emulsion made according to the methods and processes described herein is also a microemulsion, inasmuch as the emulsified droplets of non-polar compounds have a particle size, such as a mean or median particle size, in the micrometer range, such as about 10 μm or less or even 5 μm or less. Further, because of the low amount of surfactant used to prepare the lipid component, the emulsion has a very low amount of surfactant. Yet because of the large amount of non-polar compounds added to the lipid phase, the emulsion still has a large amount of the non-polar compound, such as a large amount of omega fatty acids. For example, the emulsion can contain from about 20% to about 80% by weight fatty acids, with less than 5-10% surfactant.

Summary of Terms

The invention will now be described in detail by way of reference only using the following definitions and examples. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

As used herein, the singular forms "a," "an" and "the" include plural referents unless the context clearly dictates otherwise.

Ranges or values can be expressed herein as from "about" one particular value, and/or to "about" another particular value. When such a range is expressed, another aspect includes from the one particular value of the range and/or to the other particular value of the range. It will be further understood that the endpoints of each of the ranges are significant both in relation to the other endpoint, and independently of the other endpoint. Similarly, when values are expressed as approximations, by use of the antecedent "about," it will be understood that the particular value forms another aspect. In certain example embodiments, the term "about" is understood as within a range of normal tolerance in the art for a given measurement, for example, such as within 2 standard deviations of the mean. In certain example embodiments, depending on the measurement "about" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about. Further, terms used herein such as "example," "exemplary," or "exemplified," are not meant to show preference, but rather to explain that the aspect discussed thereafter is merely one example of the aspect presented.

As used herein, the term "additive" includes any component that can be added to foodstuffs or other consumable product to enhance one or more of its nutritional, pharmaceutical, dietary, health, nutraceutical, pharmaceutical, health benefit, energy-providing, treating, taste, shelf-life, holistic properties, or other properties. Certain additives that may be used with the methods and compositions described herein include, for example, stabilizers and humectants such as glycerin; pH adjusters such as citric, ascorbic acid, and malic acid; sweeteners such as xylitol, erythritol, and/or other sugar alcohols; consumable flavoring agents; consumable coloring agents; and, preservatives such as sorbic acid, potassium sorbate, sodium benzoate and other natural antimicrobial derived from fruit which has bioflavonoids and organic acids; essential oils; and fragrances. Other additives known to those skilled in the art can also be added based on, for example, the intended use of the finished product.

As used herein "tocopherol" refers to the four different forms of the Vitamin E family represented by the formula below:

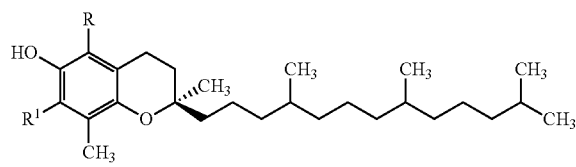

For alpha-tocopherol R and $R^1$=$CH_3$, beta-tocopherol R=$CH_3$ and $R^1$=H, gamma-tocopherol R=H and $R^1$=$CH_3$, and delta-tocopherol R and $R^1$=H. Each isomer can be present alone or in combination with the other isomers.

As used herein "tocotrienol" refers to the four different forms of the Vitamin E family represented by the formula below.

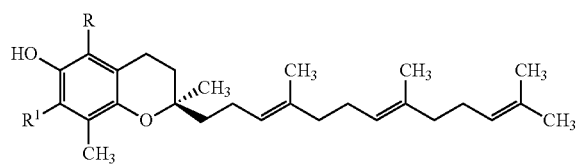

For alpha-tocotrienol R and $R^1$=$CH_3$, beta-tocotrienol R=$CH_3$ and $R^1$=H, gamma-tocotrienol R=H and $R^1$=$CH_3$, and delta-tocotrienol R and $R^1$=H. Each isomer can be present alone or in combination with the other isomers.

Disclosed herein is the use of d-α-tocopheryl polyethylene glycol 1000 succinate (TPGS) having the formula:

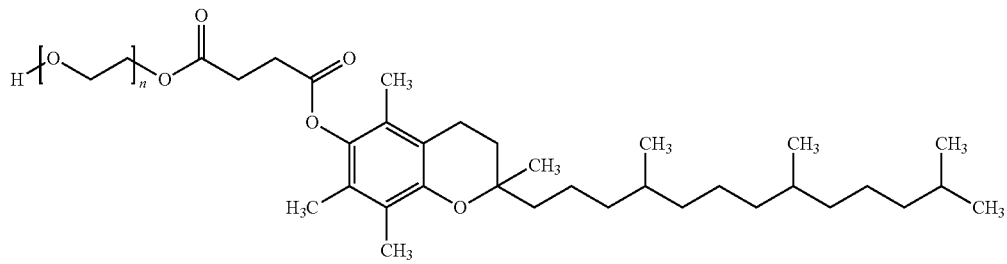

wherein the index n has an average value of 25.

Disclosed herein are TPGS "derivatives." The derivatives can vary by the number of ethyleneoxy units, for example, n=50, or by substituting a tocotrienol unit for the tocopherol.

As used herein, "colloid" refers to a mixture containing two phases, a dispersed phase and a continuous phase, the dispersed phase containing particles (droplets) distributed throughout the continuous phase. Colloidal mixtures include aerosols, foams and dispersions, for example, emulsions, for example, nanoemulsions. A liquid colloid, for example, a nanoemulsion, can have a similar appearance, for example, clarity, to a solution in which there is no dispersed phase.

As used herein the term "emulsion" refers to a colloidal dispersion of two immiscible liquids, for example, an oil (lipid) in water colloid (O/W), a water in oil colloid (W/O), an oil in water in oil colloid (O/W/O) or a water in oil in water colloid (W/O/W). In the oil in water emulsion, a hydrophobic phase (oil) is dispersed in an aqueous phase (water). one of which is part of a continuous phase and the other of which is part of a dispersed phase. The provided liquid dilution compositions include emulsions, typically oil-in-water nanoemulsions (which include any oil soluble phase dispersed in any aqueous phase, also called the water phase), in which the oil phase is the dispersed phase and the water phase is the continuous phase.

As used herein the term "median particle size" refers to the average diameter of the droplets that are dispersed in the nonpolar (oil) phase of the disclosed dispersions. "Particle Size Distribution D50" is also known as the median diameter or the medium value of the particle size distribution. This is the value of the particle diameter at 50% in the cumulative distribution. For example, if D50.5.8 μm, then 50% of the particles in the sample are larger than 5.8 μm, and 50% smaller than 5.8 μm. The median particle size and/or the particle size distribution can be determined by any method chosen by the formulator. In certain example embodiments, the particle size may be a "mean" particle size of the droplets that are dispersed in the nonpolar (oil) phase of the disclosed dispersions. For example, the mean particle size may be a volume weighted mean.

As used herein, the term "high shear," such as used in the context of high shear mixing, refers to mixing in which a force is used to push a part of an object (such as an oil droplet) in one direction and another part of the object in a different direction (i.e., a shear force). As those skilled in the art will appreciate, a high shear mixer typically uses a rotor, rotating at high speeds, to direct material outwards towards a stationary stator, thus shearing the material. Variable rotor speeds provide the ability to uniquely tailor the amount of shear energy for each application. High shear mixing can be used for homogenization, dispersion, emulsification or particle size reduction. For example, high shear mixing can be used to disperse oil into water (or other aqueous phase) by shearing the oil droplets into smaller and smaller droplets.

Example Embodiments

In certain example embodiments, disclosed herein is a process for forming an emulsion, comprising combining under high shear mixing:
a) a lipid component comprising:
  i) less than about 15% by weight of d-α-tocopheryl polyethylene glycol 1000 succinate (TPGS) or derivatives thereof, and
  ii) at least one or more non-polar compounds; and
b) an aqueous component comprising:
  i) less that about 15% by weight of one or more emulsifiers, and
  ii) the balance one or more carriers;
wherein the emulsion comprises at least about 20% by weight of the one or more non-polar compounds and wherein the emulsion comprises lipid-component droplets having a median or mean particle size less than or equal to 5 μm.

In certain example embodiments, provided is a method for providing an emulsion, comprising providing a first mixture, wherein the first mixture comprises less than about 15% by weight of TPGS or derivative thereof and a non-polar compound or mixture of non-polar compounds. The method also includes providing a second mixture, wherein the second mixture comprises water and one or more emulsifiers and wherein the one or more emulsifiers comprise less than about 15% of the second mixture. Thereafter, the first mixture can be combined with the second mixture under high shear to form an emulsion of the non-polar compound or mixture of non-polar compounds. The non-polar compounds or mixture thereof are present in droplets having a particle size of about 5 μm or less and wherein the non-polar compounds or mixture thereof comprise at least about 20% by weight of the emulsification.

The droplets formed by the disclosed process and method, also referred to herein interchangeably as "micelles" or "particles" have an average diameter of less than or equal to 5 μm. In certain example embodiments the average diameter is less than or equal to 4.5 μm. In certain example embodiments, the average diameter is less than or equal to 4 μm. In a further embodiment the average diameter is less than or equal to 3.5 μm. In further embodiments the average diameter is less than or equal to 3 μm. In a yet another embodiment the average diameter is less than or equal to 2.5 μm. In a still yet further embodiment the average diameter is less than or equal to 2 μm. In a still yet another embodiment the average diameter is less than or equal to 1.5 μm. In a yet still further embodiment the average diameter is less than or equal to 1 μm. The average diameter can have any value from 5 nanometers (nm) to 5 μm. The average diameter can have any value in the recited range. For example, in the range 5 nm to 100 nm, the average can be any value, i.e., 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 55 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 nm, 94 nm, 95 nm, 96 nm, 97 nm, 98 nm, 99 nm and 100 nm.

The droplets formed by the disclosed method and process, also referred to herein interchangeably as "micelles" or "particles," have a particle size distribution, D50, from about 50 nm to about 5 μm. In one embodiment the particle size distribution, D50, from about 50 nm to about 5 μm. In another embodiment the particle size distribution, D50, from about 100 nm to about 5 μm. In a further embodiment the particle size distribution, D50, from about 100 nm to about 1 μm. In a still further embodiment the particle size distribution, D50, from about 1 μm to about 5 μm. In a yet another embodiment the particle size distribution, D50, from about 250 nm to about 1 μm. In a still yet further embodiment the particle size distribution, D50, from about 1 μm to about 5 μm. In a still yet another embodiment the particle size distribution, D50, from about 500 nm to about 5 μm. In a yet still further embodiment the particle size distribution, D50, from about 500 nm to about 1 μm. In yet still further embodiments, the particle size distribution, D50, is about 0.3 μm, 0.4 μm, 0.5 μm, 0.6 μm, 0.7 μm, 0.8 μm, 0.9 μm, 1.0 μm, 1.5 μm, 2.0 μm, 2.5 μm, 3.0 μm, 3.5 μm, 4.0 μm, 4.5 μm, or 5.0 μm.

In certain example embodiments, the particle size distribution, D50, can have any value from 5 nanometers (nm) to 5 μm in the recited range. For example, in the range 50 nm to 1 μm, the average can be any value, i.e., 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 550 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, 810 nm, 820 nm, 830 nm, 840 nm, 850 nm, 860 nm, 870 nm, 880 nm, 890 nm, 900 nm, 910 nm, 920 nm, 930 nm, 940 nm, 950 nm, 960 nm, 970 nm, 980 nm, 990 nm and 1 μm.

When the average particle size or particle size distribution is in the range of from about 10 nm to about 100 nm the droplets for what is referred to herein as "nano-emulsions." The disclosed nano-emulsions contain micelles and can contain one or more surfactants surrounding a non-polar active ingredient, which is dispersed in the water phase. The surfactants are disclosed herein below.

Particle size can be determined by a variety of conventional methods. In certain example embodiments, Light Amplification by Stimulated Emission of Radiation using MalvernSize LASER Diffractor (e.g., Model S and Model 2000 instruments) can be used to determine particles size.

In certain example embodiments, emulsions are oil-in-water emulsions, i.e., are colloidal dispersions of an immiscible organic phase in an aqueous phase wherein the immiscible organic phase is continuous and equally dispersed. The droplets of the disclosed emulsions can have the average particle size or particle size distribution as described herein.

In certain example embodiments of the disclosed process the "at least one or more non-polar compounds" of section (a)(ii) comprises one or more "unsaturated fatty acids." The unsaturated fatty acids can be in the form of mono-, di- and triglycerides or fatty acid esters, for example, ethyl esters, or derivatives thereof.

In certain example embodiments of the disclosed method and process the source of the unsaturated fatty acids is derived from fish oils. The source of the fish oils can be from any type of fish, typically "oily fish" or from algal sources. Non-limiting examples of oily fish include salmon, herring, mackerel, anchovies and sardines, however, the fish oil can be obtained from any fish which provides the required profile of nutritionally important unsaturated fatty acids.

In certain example embodiments of the disclosed method and process, the unsaturated fatty acids can be obtained from vegetable sources, for example, vegetable oils. Non-limiting examples of vegetable oils includes coconut oil, corn oil, cottonseed oil, olive oil, palm oil, peanut oil, canola oil, safflower oil, sesame oil, soybean oil and sunflower oil. Any edible oil, however, including oils obtained from nuts, can be used as a component of the non-polar compounds in this embodiment.

In certain example embodiments, an admixture of one or more fish oils and vegetable oils can be used. In one example, fatty acid mono-, di- or triglycerides and fatty acid esters easily obtained from vegetable oils, for example, oleic, linolenic and linoleic fatty acids can be added to enhance the amount of "unsaturated fatty acids" that comprise the "at least one or more non-polar compounds" of section (a)(ii)." Non-limiting examples of fatty acids derived from fish oil include the omega-3 fatty acids, omega-5 fatty acids, omega-6 fatty acids, omega-7 fatty acids, and mixtures thereof, particularly eicosapentaenoic acid (EPA), docosahexaenoic acid (DHA) and arachidonic acid (AA).

In certain example embodiments of this aspect d-α-tocopheryl polyethylene glycol 1000 succinate (TPGS) is used as the component of section (a)(i). In another embodiment, derivatives of TPGS can be used either alone or in combination with TPGS or other derivatives. Non-limiting examples of TPGS derivatives includes d-α-tocopheryl polyethylene glycol 2000 succinate (TPGS$_{2k}$) and d-α-tocopheryl polyethylene glycol 1500 succinate. In certain examples embodiments, the TPGS of the lipid component of the process is less than about 15%, 14%, 13%, 12%, 11%, 10%, 9%, 8%, 7%, 6%, or 5%. In certain examples embodiments, the TPGS of the first reaction mixture is less than about 15%, 14%, 13%, 12%, 11%, 10%, 9%, 8%, 7%, 6%, or 5%. In certain example embodiments, the TPGS comprises less than about 10%, 9%, 8%, 7%, 6%, or 5% of the emulsion resulting from the methods and processes described herein.

As those skilled in the art will appreciate, any high shear mixers known in the art can be used to achieve the high shear mixing described herein. Example high shear mixers include those supplied under the brands "TK Products Homomic Line Mill" or "Bematek" or "Greerco" or "Ross." Example suppliers include IKA WORKS, Kady International, Charles Ross and Son Company, Silverson Machines, and Pulsar. A specific mixer that can be used in accordance with the methods and processes described herein is the Ross™ HSM-405SC-25 high shear mixer. In certain example embodiments, the rotor speed of the mixer is around 3,600 revolutions per minutes (rpm), such as around 1,400 rpm, 1,600 rpm, 1,800 rpm, 2,000 rpm, 2,200 rpm, 2,400 rpm, 2,600 rpm, 2,800 rpm, 3,000 rpm, 3,200 rpm, 3,400 rpm, 3,600 rpm, 3,800 rpm, 4,000 rpm, 4,200 rpm, 4,400 rpm, 4,600 rpm, 4,800 rpm, 5,000 rpm, 5,200 rpm, 5,400 rpm, 5,600 rpm or higher. In certain example embodiments, the rotor speed of the mixer is between 2,000 rpm to 6,000 rpm. In certain example embodiments, the rotor speed is between 3,000 rpm and 5,000 rpm. In certain example embodiments, the rotor speed is between 3,000 rpm and 4,000 rpm. With such high shear mixing, for example, hygroscopic emulsifiers can be mixed into the aqueous phase. Further, the high shear mixing emulsifies the lipid phase with the aqueous phase to form the final emulsion, in accordance with the methods and processes provided herein.

Emulsifiers

In the disclosed process the one or more emulsifiers can be chosen from any emulsifiers that provides the desired median or mean particle size of the resulting droplets. One category of emulsifiers includes, for example, $C_{14}$-$C_{22}$ fatty alcohols non-limiting examples of which are chosen from 1-tetradecanol (myristyl alcohol), 1-hexadecanol (cetyl alcohol), cis-9-hexadecen-1-ol (plamitoleyl alcohol), 1-octadecanol (stearyl alcohol), cis-9-octadecen-1-ol (oleyl alcohol), trans-9-octadecen-1-ol (elaidyl alcohol), 1-eicosanol (arachidyl alcohol), and 1-docosanol (behenyl alcohol). Further non-limiting examples of emulsifiers include esters of $C_{14}$-$C_{22}$ fatty alcohols and inorganic acids chosen from di-1-tetradecanyl phosphate (di-myristyl phosphate), di-1-hexadecanyl phosphate (di-cetyl phosphate), di-cis-9-hexadecen-1-yl phosphate (di-plamitoleyl phosphate), di-1-octadecanyl phosphate (di-stearyl phosphate), di-cis-9-octadecen-1-yl phosphate (di-oleyl phosphate), di-trans-9-octadecen-1-yl phosphate (di-elaidyl phosphate), di-1-eicosanyl phosphate (di-arachidyl phosphate), di-1-docosanyl phosphate (di-behenyl phosphate), 1-tetradecanyl sulfate (myristyl sulfate), 1-hexadecanyl sulfate (cetyl sulfate), cis-9-hexadecen-1-yl sulfate (plamitoleyl sulfate), 1-octadecanyl sulfate (stearyl sulfate), cis-9-octadecen-1-yl sulfate (oleyl sulfate), trans-9-octadecen-1-yl sulfate (elaidyl sulfate), 1-eicosanyl sulfate (arachidyl sulfate), and 1-docosanyl sulfate (behenyl sulfate).

Another category of emulsifiers includes, for example, glyceryl monostearate, glyceryl monopalmitate, glyceryl monooleate, etc.; monostearin, monopalmitin, monoolein, Lactic acid esters of mono- and diglycerides of fatty acids, citric acid esters of mono- and diglycerides of fatty acids, mono- and diacetyl tartaric acid esters of mono- and diglycerides of fatty acids, sucrose esters of fatty acids, i.e., mono-, di- and triesters of sucrose with fatty acids.

A further category of emulsifiers includes fatty acid esters of propane-1,2-diol. Non-limiting examples include 1-hydroxypropan-2-yl dodecanoate, 2-hydroxypropyl dodecanoate, propane-1,2-diyl didodecancoate, 1-hydroxypropan-2-yl tetradecanoate, 2-hydroxypropyl tetradecanoate, propane-1,2-diyl ditetradecancoate, 1-hydroxypropan-2-yl hexadecanoate, 2-hydroxypropyl hexadecanoate, and propane-1,2-diyl dihexadecancoate.

A still further category of emulsifiers includes $C_8$-$C_{18}$ alkylglycosides having the formula:

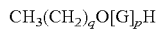

wherein G represents a monosaccharide residue chosen from glucose, fructose, mannose, galactose, talose, allose, altrose, idose, arabinose, xylose, lyxose, ribose and mixtures thereof, the index p is from 1 to 4, the index q is from 7 to 17. The following are non-limiting examples of alkyl glucoside surfactants include (2R,3S,4S,5R,6R)-2-(hydroxymethyl)-6-octooxyoxane-3,4,5-triol (octyl glucoside, n-octyl-b-D-glucoside), (2R,3R,4S,5S,6R)-2-decoxy-6-(hydroxymethyl)tetra-hydropyran-3,4,5-triol (decyl glucoside, n-decyl-b-D-glucoside), and (2R,3R,4S,5S,6R)-2-dodecoxy-6-(hydroxymethyl)tetrahydropyran-3,4,5-triol (dodecyl glucoside, lauryl glucoside, n-dodecyl-b-D-glucoside). One example of a suitable admixture of $C_8$-$C_{16}$ alkylglycosidyl nonionic surfactants is PLANTACARE™ 818 UP available from Cogins Chemical Co.

A still another category of emulsifiers includes polyoxyethylene glycol alkyl ethers having the formula:

wherein R is a linear or branched alkyl group having from 6 to 20 carbon atoms and n is an integer of about 2 to about 20.

One example of suitable ethoxylate alcohols is the NEODOL™ ethoxylated alcohols from Shell Chemicals. NEODOL™ 23-1 comprises a mixture of R units that are $C_{12}$ and $C_{13}$ in length with an average of 1 ethoxy unit. Non-limiting examples of ethoxylated alcohols include NEODOL™ 23-1, NEODOL™ 23-2, NEODOL™ 23-6.5, NEODOL™ 25-3, NEODOL™ 25-5, NEODOL™ 25-7, NEODOL™ 25-9, PLURONIC™ 12R3, and PLURONIC™ 25R2 available from BASF.

In certain example embodiments, the emulsifier includes polyoxyethylene glycol alkyl ethers having the formula:

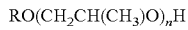

wherein R is a linear or branched alkyl group having from 6 to 20 carbon atoms and n is an integer of about 2 to about 20.

In certain example embodiments, the emulsifier includes polyoxyethylene polyoxypropylene block copolymers known as "poloxamers" having the formula:

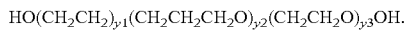

These are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol. These are also well known by the trade name PLURONICS™. These compounds are commonly named with the word Poloxamer followed by a number to indicate the specific co-polymer, for example Poloxamer 407 having two PEG blocks of about 101 units ($y^1$ and $y^3$ each equal to 101) and a polypropylene block of about 56 units. This category of emulsifiers is commercially available, for example, under the trade name LUTROL™ F-17 available from BASF.

A further example of emulsifiers includes alkyl amides that are ethoxylate, propoxylated, or mixtures thereof, having the formula:

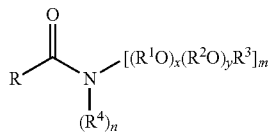

wherein R is $C_7$-$C_{21}$ linear alkyl, $C_7$-$C_{21}$ branched alkyl, $C_7$-$C_{21}$ linear alkenyl, $C_7$-$C_{21}$ branched alkenyl, and mixtures thereof. $R^1$ is ethylene; $R^2$ is $C_3$-$C_4$ linear alkylene, $C_3$-$C_4$ branched alkylene, and mixtures thereof; in some iterations $R^2$ is 1,2-propylene. Emulsifires that comprise a mixture of $R^1$ and $R^2$ units can comprise from about 4 to about 12 ethylene units in combination with from about 1 to about 4 1,2-propylene units. The units can be alternating or grouped together in any combination suitable to the formulator. In one iteration, the ratio of $R^1$ units to $R^2$ units is from about 4:1 to about 8:1. In another iteration, a $R^2$ unit (i.e., 1,2-propylene) is attached to the nitrogen atom followed by the balance of the chain comprising from 4 to 8 ethylene units.

$R^3$ is hydrogen, $C_1$-$C_4$ linear alkyl, $C_3$-$C_4$ branched alkyl, and mixtures thereof; preferably hydrogen or methyl, more preferably hydrogen.

$R^4$ is hydrogen, $C_1$-$C_4$ linear alkyl, $C_3$-$C_4$ branched alkyl, and mixtures thereof. When the index m is equal to 2 the index n must be equal to 0 and the $R^4$ unit is absent and is instead replaced by a —$[(R^1O)_x(R^2O)_yR^3]$ unit.

The index m is 1 or 2, the index n is 0 or 1, provided that when m is equal to 1, n is equal to 1; and when m is 2 n is 0; in one example, m is equal to 1 and n is equal to one, resulting in one —$[(R^1O)_x(R^2O)_yR^3]$ unit and $R^4$ being present on the nitrogen. The index x is from 0 to about 50, in one embodiment from about 3 to about 25, in another embodiment x is from about 3 to about 10. The index y is from 0 to about 10, in one example y is 0; however, when the index y is not equal to 0, y is from 1 to about 4. In one embodiment all of the alkyleneoxy units are ethyleneoxy units.

Surfactants

The disclosed emulsions can be further stabilized by the addition of one or more surfactants and/or co-surfactants and/or emulsion stabilizers. Without wishing to be limited by theory, surfactants are believed to form an interfacial film between the oil and water phase of the emulsion thereby providing stability. The following are non-limiting examples of surfactants suitable for use in preparing the disclosed emulsions.

Alkyl Sulfates

The disclosed compositions can comprise one or more $C_{10}$-$C_{20}$ primary, branched chain and random alkyl sulfates having the formula $ROSO_3M$ wherein R is a linear or branched chain comprising from 10 to 20 carbon atoms and M represents a water soluble cation. Non-limiting examples of alkyl sulfates suitable for use in the disclosed compositions include sodium decylsulfate, sodium dodecylsulfate, sodium tetradecylsulfate, sodium hexadecylsulfate, and sodium octadecylsulfate.

Alkyl Alkoxy Sulfates

The disclosed compositions can comprise one or more $C_{10}$-$C_{18}$ alkyl alkoxy sulfates having the formula:

wherein the index x is from 9 to 17, y is from 1 to 7 and M is a water soluble cation chosen from ammonium, lithium, sodium, potassium and mixtures thereof. A non-limiting example includes sodium dodecyl diethoxy sulfate having the formula:

Alkyl alkoxy sulfates are also commercially available as a mixture of ethoxylates, for example, sodium laureth sulfate is available as a mixture of ethoxylates, i.e., the index y is from 2 to 4. Other suitable examples include sodium laureth-2 sulfate having an average of 2 ethoxylates and a $C_{12}$ linear alkyl chain. Sodium laureth-2 is available as Texapon™ N 56 from Cognis Corp. Further examples of alkyl alkoxy sulfates includes sodium laureth-1 sulfate, sodium laureth-3 sulfate, sodium laureth-4 sulfate, sodium myreth-2 sulfate and sodium myreth-3 sulfate.

Alkenyl Sulfonates

The disclosed compositions can comprise one or more $C_{10}$-$C_{18}$ alkenyl sulfonates (α-olefin sulfonates) having the formula:

wherein the index z is from 7 to 15 and M is a water soluble cation chosen from ammonium, lithium, sodium, potassium and mixtures thereof. Olefin sulfonates are commercially available as a mixture of alkenyl chains, for example, sodium $C_{14}$-$C_{16}$ olefin sulfonate Bio-Terge™ AS-40 available from Stepan. Further non-limiting examples of alkenyl sulfonates include $C_{12}$-$C_{16}$ olefin sulfonates and $C_{14}$-$C_{18}$ olefin sulfonates. Another example is $C_{12}$-$C_{15}$ pareth-15 sulfonate available as Avanel™ S 150 CG.

Alkyl Alkoxy Carboxylates

The disclosed compositions can comprise one or more $C_{10}$-$C_{18}$ alkyl alkoxy carboxylates having the formula:

wherein the index x is from 9 to 17, y is from 1 to 5 and M is a water soluble cation chosen from ammonium, lithium, sodium, potassium and mixtures thereof. A non-limiting example includes sodium dodecyl diethoxy carboxylate having the formula:

Alkyl alkoxy carboxylates are also commercially available as a mixture of ethoxylates, for example, sodium laureth sulfate is available as a mixture of ethoxylates, i.e., the index y is from 2 to 4. Other suitable examples include sodium laureth-2 sulfate having an average of 2 ethoxylates and a $C_{12}$ linear alkyl chain. Sodium laureth-2 is available as Texapon™ N 56 from Cognis Corp. Further examples of alkyl alkoxy sulfates include sodium laureth-1 sulfate, sodium laureth-3 sulfate, sodium laureth-4 sulfate, sodium myreth-2 sulfate and sodium myreth-3 sulfate.

Isethionate Esters of Alkyl Alkoxy Carboxylic Acids

The disclosed compositions can comprise one or more $C_{10}$-$C_{18}$ isethionate esters of alkyl alkoxy carboxylates having the formula:

wherein the index x is from 9 to 17, the index y is from 1 to 5 and M is a water soluble cation. Isethionate esters of alkyl alkoxy carboxylates are described in U.S. Pat. No. 5,466,396 the disclosure of which is included herein by reference in its entirety.

Alkyl Carboxyamides

The disclosed compositions can comprise one or more $C_{10}$-$C_{18}$ alkyl carboxyamides having the formula:

wherein R is hydrogen or methyl the index x is from 9 to 17, the index y is from 1 to 5 and M is a water soluble cation. A non-limiting example of an alkyl carboxyamide suitable for use in the disclosed compositions includes potassium cocoyl glycinate available as AMILITE™ GCK-12 from Ajinomoto. A further example includes compounds wherein R is methyl, for example, sodium cocoyl sarcosinate.

The following are non-limiting examples of zwitterionic surfactants suitable for use in preparing the disclosed emulsions.

Alkyl Amide Betaines

One category of zwitterionic surfactants relates to $C_{10}$-$C_{16}$ alkyl amide betaines having the formula:

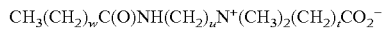
$$CH_3(CH_2)_wC(O)NH(CH_2)_uN^+(CH_3)_2(CH_2)_tCO_2^-$$

wherein the index w is from 9 to 15, the index u is from 1 to 5 and the index t is from 1 to 5. Non-limiting examples of betaine surfactants includes {[3-(decanoylamino)ethyl]-(dimethyl)-ammonio}acetate, {[3-(decanoylamino)ethyl](dimethyl)ammonio}-acetate, {[3-(dodecanoyl-amino)ethyl](dimethyl)ammonio}acetate, {[3-(dodecanoylamino)propyl]-(dimethyl)-ammonio}acetate, {[3-(dodecanoylamino)-butyl](dimethyl)ammonio}acetate, {[3-(tetra-decanoylamino)ethyl](dimethyl)-ammonio}acetate, {[3-(tetradecanoylamino)-propyl](dimethyl)ammonio}acetate, {[3-(hexadecanoylamino)ethyl](dimethyl)-ammonio}acetate, and {[3-(hexa-decanoylamino)propyl](dimethyl)ammonio}acetate.

Alkyl Amide Sultaines

Another category of zwitterionic surfactants relates to $C_{10}$-$C_{16}$ alkyl amide sultaines having the formula:

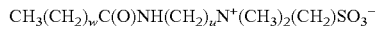
$$CH_3(CH_2)_wC(O)NH(CH_2)_uN^+(CH_3)_2(CH_2)_tSO_3^-$$

wherein the index w is from 9 to 15, the index u is from 1 to 5 and the index t is from 1 to 5. Non-limiting examples of sultaine surfactants includes {[3-(decanoylamino)ethyl]-(dimethyl)-ammonio}methanesulfonate, {[3-(decanoylamino)ethyl](dimethyl)ammonio}-methanesulfonate, {[3-(dodecanoyl-amino)ethyl](dimethyl)ammonio}methanesulfonate, {[3-(dodecanoylamino)-propyl](dimethyl)ammonio}methanesulfonate, {[3-(dodecanoyl-amino)butyl](dimethyl)-ammonio}methanesulfonate, {[3-(tetradecanoylamino)ethyl]-(dimethyl)ammonio}methane-sulfonate, {[3-(tetradecanoylamino)propyl](dimethyl)-ammonio}methanesulfonate, {[3-(hexadecanoylamino)ethyl](dimethyl)ammonio}-methanesulfonate, and {[3-(hexadecanoylamino)propyl](dimethyl)ammonio}-methanesulfonate.

Alkyl Hydroxy Sultaines

A further category of zwitterionic surfactants relates to $C_{10}$-$C_{16}$ alkyl hydroxy sultaines having the formula:

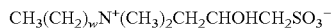
$$CH_3(CH_2)_wN^+(CH_3)_2CH_2CHOHCH_2SO_3^-$$

wherein the index w is from 9 to 15. Non-limiting examples of alkyl hydroxy sultaine surfactants includes 3-[dodecyl(dimethyl)azaniumyl]-2-hydroxypropane-1-sulfonate (lauryl hydroxysultaine), 3-[tetradecyl(dimethyl)azaniumyl]-2-hydroxypropane-1-sulfonate (myristyl hydroxysultaine), (Z)-{dimethyl[3-(octadec9-enamido)propyl]ammonio}-methanesulfonate (oleyl hydroxysultaine), and the like.

Carriers

Included within the components of the aqueous phase described herein are carriers. In certain example embodiments, the disclosed aqueous phase can comprise from about 0.01% to about 90% by weight of one or more carriers.

In certain example embodiments, the aqueous phase can comprise from about 85% to about 99% by weight of water. In one embodiment, the compositions comprise from about 85% to about 95% by weight of one or more carriers. In one embodiment, water is the sole carrier. In a further example, water comprises from about 87% to about 99% by weight of the carrier. In a still further examples water comprises from about 90% to about 95% by weight of the carrier. In one embodiment the carrier can also comprise one or more alcohols. Non-limiting examples of suitable alcohols include ethanol, n-propanol, iso-propanol, and propanediol. The formulator can, however, choose any mixture of water soluble organic solvents and/or water.

In another example embodiment, disclosed herein is a process for forming an emulsion, comprising combining under high shear mixing:
a) a lipid component comprising:
   i) less than about 15% by weight of d-α-tocopheryl polyethylene glycol 1000 succinate (TPGS) or derivatives thereof, and
   ii) at least one or more non-polar compounds; and
b) an aqueous component comprising:
   i) less that about 15% by weight of one or more emulsifiers,
   ii) one or more adjunct ingredients, and
   iii) the balance one or more carriers;
wherein the emulsion comprises at least about 20% by weight of the one or more non-polar compounds and wherein the emulsion comprises lipid-component droplets having a mean particle size or median particle size less than or equal to about 5 μm.

Additives

In certain example embodiments, the compositions provided herein can include one or more additives. For example, the compositions may include one or more adjunct components or additives are also included, such as vitamins. The vitamins can be added directly, for example, tocopherol, or the vitamin can be added in a releasable form, for example, ascorbyl palmitate. Other suitable adjunct components include thickening agents, for example, starches, vegetable gums, pectin or proteins. Non-limiting examples of thickening agents include alginic acid (E400), sodium alginate (E401), potassium alginate (E402), ammonium alginate (E403), calcium alginate (E404), agar (E406), carrageenan (E407), locust bean gum (E410) pectin (E440), gelatin (E441) and xanthan gum. Other adjunct components or additives include essential oils, fragrances, flavorants, and colorants.

In certain example embodiments, the additives are added during preparation of aqueous phase as described herein. For example, polar additives can be added to a polar carrier such as water. The water/additive mixture can then be included within the resultant compositions when the aqueous phase is combined with the lipid phase as described herein. In certain example embodiments, one or more additives may be added to the emulsion after the lipid phase is mixed with the aqueous phase as described herein. That is, the one or more additives can be added to emulsion after the emulsion is prepared.

Compositions

In certain example embodiments, provided is an oil-in-water emulsion composition, such as an emulsion produced by the processes or methods described herein. For example, the emulsion can include a lipid component, an emulsifier, a surfactant, as described herein. The lipid component of the oil-in-water emulsion can be any nonpolar compound as described herein, such as an omega fatty acid. For example, the composition can include omega-3 fatty acids, omega-5 fatty acids, omega-6 fatty acids, omega-7 fatty acids. In other example compositions, the oil is a flaxseed oil or other seed oil. The lipids, for example, can comprise a substantial amount of the total composition. For example, the lipids can comprise about 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%%, 21%, 20%, 19%, 18%, 17%, 16%, or 15% of the emulsion.

Additionally, the lipid component is present in small droplets or "particles" as described herein. The particles, for example, can be any size described herein. As an example, the lipid particles of the composition have an average diameter of less than or equal to about 5 µm. In certain example embodiments, the average diameter is less than or equal to 4.5 µm. In certain example embodiments, the average diameter is less than or equal to 4 µm. In a further example embodiment the average diameter is less than or equal to 3.5 µm. In further embodiments the average diameter is less than or equal to 3 µm. In a yet another embodiment the average diameter is less than or equal to 2.5 µm. In a still yet further embodiment the average diameter is less than or equal to 2 µm. In a still yet another embodiment the average diameter is less than or equal to 1.5 µm. In a yet still further embodiment the average diameter of the particles in the emulsion is less than or equal to about 1 µm. In certain example embodiments, about 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, or 35% of the lipid particles of the emulsion are less than about 5 µm, 4 µm, 3 µm, 2 µm, or 1 µm in size.

In certain example embodiments, the emulsion composition can include an emulsifier. The emulsifier can be any of the emulsifiers described herein. That is, the emulsifier can be any emulsifier identified herein that can, when used according to the methods and processes described herein, provide the desired median or mean particle size of the resulting droplets. The emulsifier, for example, can be present in the emulsion in an amount that is less than about 10% of the emulsion, such as about 10%, 9%, 8%, 7%, 6%, 5%, 4%, 3%, 2%, or 1% of the emulsion.

In certain example embodiments, the emulsion composition can additionally include a surfactant. The surfactant can be any surfactant described herein. Example surfactants include, for example, an alkyl sulfate, alkyl alkoxy sulfate, alkenyl sulfonate, alkyl alkoxy carboxylate, isethionate esters of alkyl alkoxy carboxylic acids, alkyl carboxyamide, alkyl amide betaine, alkyl amide sultaine, or alkyl hydroxy sultaine. In certain example embodiments, the surfactant is d-α-tocopheryl polyethylene glycol 1000 succinate ("TPGS") or a derivative thereof. The surfactant is present in a low amount as described herein. For example, the surfactant can comprise less than about 15%, 14%, 13%, 12%, 11%, 10%, 9%, 8%, 7%, 6%, 5%, 4%, 3%, 2%, or 1% of the emulsion. In certain example embodiments, the compositions can also include any of the carriers and/or additives as described herein.

The emulsion compositions described herein, such as a composition produced by the methods and processes described herein, can be used with and/or integrated into a variety of consumable products and foodstuffs. For example, the compositions provided herein can be used in nutraceutical products, such as fish oil or flaxseed oil health supplements. The fish oil or flaxseed oil, for example, can be included as the lipid component in the emulsion as described herein, and the prepared emulsion can be used a direct supplement. The prepared emulsion can also include additives, for example, to enhance shelf-life, flavor, and product appearance. In certain example embodiments, the emulsion compositions may be included within a pharmaceutical/nutraceutical deliver form, such as within a softgel.

Without wishing to be bound by any particular theory, and as those skilled in the art will appreciate, it is believed the small particle size of the oil droplets in the compositions/products described herein increase absorption of the lipid component. For example, if the lipid component of the lipid phase is fish oil, it is believed that the smaller particle size will increase absorption of the fish oil when the emulsion is ingested. It is believed, for example, that the small particle size increases the rate of delivery and/or bioavailability of the fish oil when the fish oil is ingested, thereby increasing the absorption of the consumed fish oil. In certain example embodiments, it is believed that use of the emulsion compositions provided herein will increase absorption by 5%, 10%, 15%, 20%, 25%, 30%, 35%, 40%, 45%, 50%, 55%, 60%, 65%, 70%, 75%, 80%, 85%, 90%, 95%, 100% or more. Although any conventional means may be used to determine absorption, in certain example embodiments fatty acid analysis via gas chromatography (GC), and/or high performance liquid chromatography (HPLC), can be performed on a blood sample from a subject after the subject has consumed the composition.

EXAMPLES

The present invention is described in further detain in the following examples which are not in any way intended to limit the scope of the invention as claimed. The following examples are offered to illustrate, but not to limit the claimed invention.

Example 1—Emulsification with 5% TPGS

To prepare a 1000 kg industrial batch of an example emulsion as described herein, with 5% TPGS, a premix was prepared as the lipid component. The premix was then mixed with an aqueous component, along with other components.

Preparation of Premix

To prepare the premix (340 kg), approximately 49.98 kg of TPGS (e.g., Antares Vitamin E TPGS NF or other TPGS suppliers) were heated to 65° C. until it transitioned from a semisolid to a liquid form. Separately, 290.02 kg of fish oil (Organic Technologies™) was weighed and then heated to 40° C. in an industrial mixer. The liquid TPGS was added to the heated fish oil. The mixer system was nitrogen flushed, and the TPGS-fish oil mixture was mixed for approximately 20 minutes (or until the mixture is a uniform consistency) to form a liquid premix. The premix is then ready to mix with the water phase, described below, or stored. In certain examples, the premix is stored before use, in which case the premix may return to a semi-solid phase. In such examples, before the premix is mixed with the water phase (as described below), the semi-solid phase premix is heated to approximately 40° C. for about 15 min in order to convert the semi-solid phase premix back to a liquid phase. The components of the premix are shown in Table 1.

TABLE 1

| Components of Premix. | |
|---|---|
| Component | Percentage |
| Fish Oil | 85.3% |
| TPGS | 14.7% |
| TOTAL BATCH | 100.00% |

Preparation of Aqueous Phase with Emulsifier

To prepare the water phase 312 kg of room-temperature water (roughly 0.3 liters) was placed into the holding tank of a high shear Ross™ HSM-405SC-25 mixer and thereafter allowed to flow through the mixing chamber of the high shear mixer. Separately, 36.0 kg of powdered emulsifier (e.g., Blue Pacific™, Tic Tim, and/or CNI™ blend) was placed into the funnel tank of the high shear mixer. Additionally, 180 kg xylitol, 0.5 kg sorbic acid, 4 kg citric acid, 6 kg Grape Color, 35 kg mixed berry flavor, 0.3 kg rosemary extract, 85 kg glycerin, 1.0 kg xanthan easy, and 0.2 kg ascorbyl palmitate were weighed. The xanthan easy and ascorbyl palmitate were added to the funnel of the Ross mixer, (along with the emulsifier, see above). The glycerin was then added to the water in the holding tank of the mixer. The mixer was then run at 65% max speed for about 5 minutes to mix the water and glycerin. The xylitol, sorbic acid, citric acid, strawberry color, passion-pineapple flavor, mixed tocopherol, and rosemary extract are then added to the water-glycerin mixture, and the combination is mixed for an additional 3-5 minutes at 65% power. The power on the Ross mixer was adjusted to 100% (approximately 3,600 rpm), and the funnel valve of the Ross mixer was fully opened to allow its contents to quickly flow in to the holding tank of the mixer. After the contents of the funnel were emptied in to the holding tank, the funnel valve was closed and mixing continues for about 5 minutes.

Preparation of Oil in Water Phase Including 5% TPGs

To prepare the final emulsified product, 340 kg of premix was slowly fed into the high shear mixer system through an intake valve of the mixer. When using a Ross mixer, for example, the T-valve valve remains approximately 70% closed (i.e., about ¼ open), thus allowing slow input of the premix into the water phase. The premix was then mixed with the water phase in the high shear mixer for approximately 25-30 minutes. The emulsified product included the components shown in Table 2, with the final product including approximately 29% fish oil and 5% TPGS.

TABLE 2

Components of 5% TPGS emulsification

| Component | Percentage |
| --- | --- |
| Water | 31.2% |
| Grape Color No. 03039 | 0.6% |
| Sorbic Acid | 0.05% |
| Xylitol | 18.0% |
| Citric Acid | 0.40% |
| Glycerin | 8.5% |
| Emulsifier | 3.6% |
| Xanthan Easy | 0.10% |
| Ascorbyl Palmitate | 0.02% |
| Mixed Berry Flavor | 3.5% |
| Rosemary Extract | 0.03% |
| Premix | 34.000% |
|  | (29% Fish Oil, 5% TPGS in final product) |
| TOTAL BATCH | 100.00% |

Following preparation of the emulsified product, a sample of the product was subjected to particle size analysis to determine the size of the non-polar (oil) component droplets within the sample. Briefly, particle size analysis was conducted using a Malvern® MasterSizer 2000 LASER diffractor. As those skilled in the art will appreciate, the Malvern® MasterSizer LASER diffractor is considered an ensemble analyzer that calculates a volume distribution from the LASER (Light Amplification by Stimulated Emission of Radiation) diffraction pattern of a suspension of particles. The raw scatter data are then processed using the manufacturer's algorithm and presented on the basis of EQUIVALENT SPHERICAL DIAMETER.

For the sample of the emulsified product using 5% TPGS in the final product, 90% of the particles (D(0.9)) had a size less than 1.088 μm, while 50% of the particles (D(0.5)) had a size smaller than 0.677 μm. Further, 10% of the particles (D(0.1)) had a size smaller than 0.390 μm. The mean particle size (volume weighted mean) was 0.713 μm. A histogram of particle size distribution for the 5% TPGS emulsification sample is shown in FIG. 1.

Example 2—Emulsification with 3% TPGS

In this example, an emulsification was prepared as described in Example 1, except that the final emulsification contained 3% TPGS. Briefly, the premix was prepared as described in Example 1, with the TPGS comprising 9.41% of the premix and the fish oil comprising the remaining 90.59% of the premix. Following preparation of the emulsification, the final emulsified product included the components shown in Table 3. Further, when 9.41% TPGS was used in the premix, the final emulsion contained 28.88% fish oil and 3% TPGS.

TABLE 3

Components of 3% TPGS emulsification

| Component | Percentage |
| --- | --- |
| Water | 35.82% |
| Grape Color No. 03039 | 0.6% |
| Sorbic Acid | 0.05% |
| Xylitol | 17.0% |
| Citric Acid | 0.40% |
| Glycerin | 7% |
| Emulsifier | 3.60% |
| Xanthan Easy | 0.10% |
| Ascorbyl Palmitate | 0.02% |
| Mixed Berry Flavor | 3.5% |
| Rosemary Extract | 0.03% |
| Premix | 31.88% |
|  | (28.88% fish oil, 3% TPGS in final product) |
| TOTAL BATCH | 100.00% |

Figure 2:
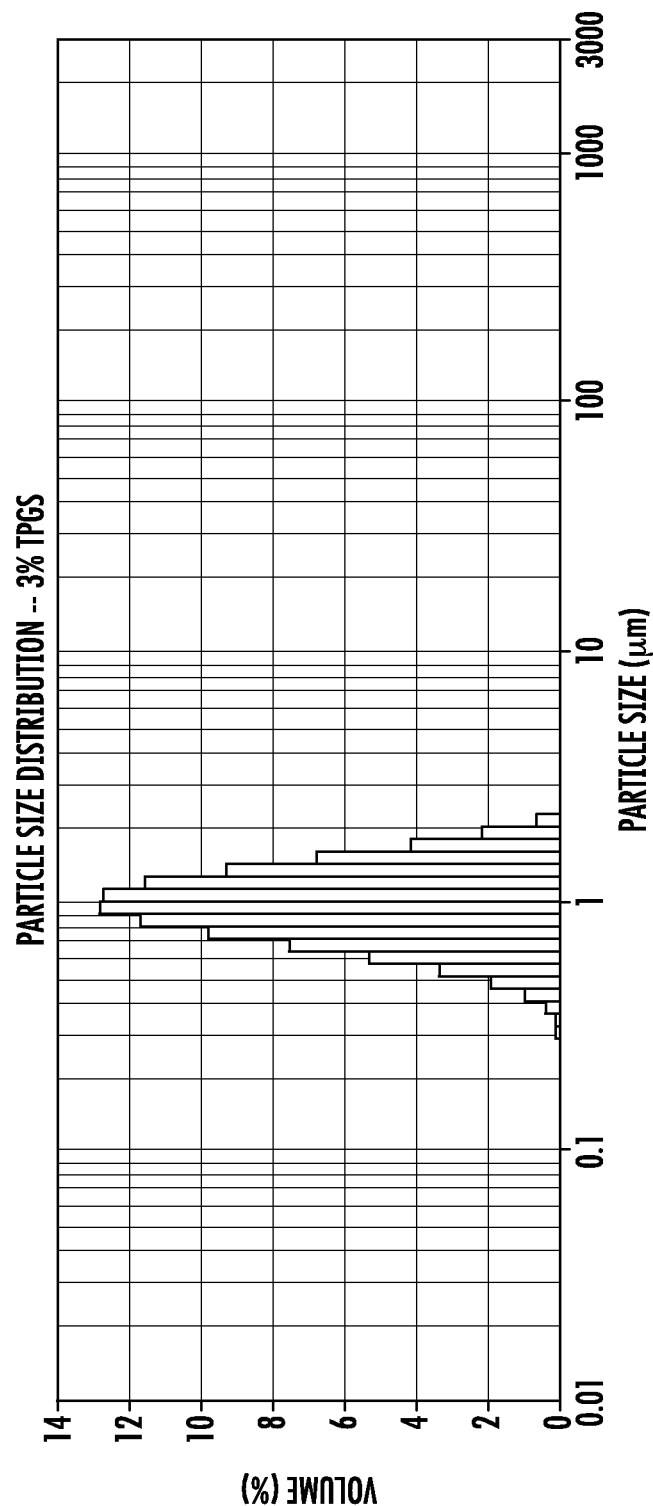
FIG. 2 is graph showing a differential histogram of particle size distribution for a sample in which 9.41% TPGS was used in the premix, in accordance with certain example embodiments. The resultant final product contained 28.88% non-polar component (oil) and 3% TPGS. The mean non-polar (oil) component particle size was 1.019 µm for the final product.

After preparation of the 3% TPGS emulsified product, a sample of the product was subjected to particle size analysis as described in Example 1 to determine the size of the non-polar (oil) component droplets within the sample. With 3% TPGS in the final emulsification, 90% of the particles (D(0.9)) had a size less than 1.490 μm, while 50% of the particles (D(0.5)) had a size smaller than 0.974 μm. Further, 10% of the particles (D(0.1)) had a size smaller than 0.614 μm. The mean particle size (volume weighted mean) was 1.019 μm. A histogram of the particle size distribution for the 3% TPGS emulsification is shown in FIG. 2.

Example 3—Emulsification with 1% TPGS

In this example, an emulsification was prepared as described in Example 1, except that the final emulsification contained 1% TPGS. Briefly, the premix was prepared as described in Example 1, with the TPGS comprising 3.35% of the premix and the fish oil comprising the remaining 96.65% of the premix. Following preparation of the emulsification, the final emulsified product included the components shown in Table 4. Further, when 3.35% TPGS was used in the premix, the final emulsion contained 28.88% fish oil and 1% TPGS.

TABLE 4

Components of 1% TPGS emulsification

| Component | Percentage |
|---|---|
| Water | 37.82% |
| Grape Color No. 03039 | 0.6% |
| Sorbic Acid | 0.050% |
| Xylitol | 17% |
| Citric Acid | 0.400% |
| Glycerin | 7% |
| Emulsifier | 3.600% |
| Xanthan Easy | 0.100% |
| Ascorbyl Palmitate | 0.02% |
| Mixed Berry Flavor | 3.5% |
| Rosemary Extract | 0.03% |
| Premix | 29.88% |
| | (28.88% fish oil, 1% TPGS in final product) |
| TOTAL BATCH | 100.00% |

Figure 3:
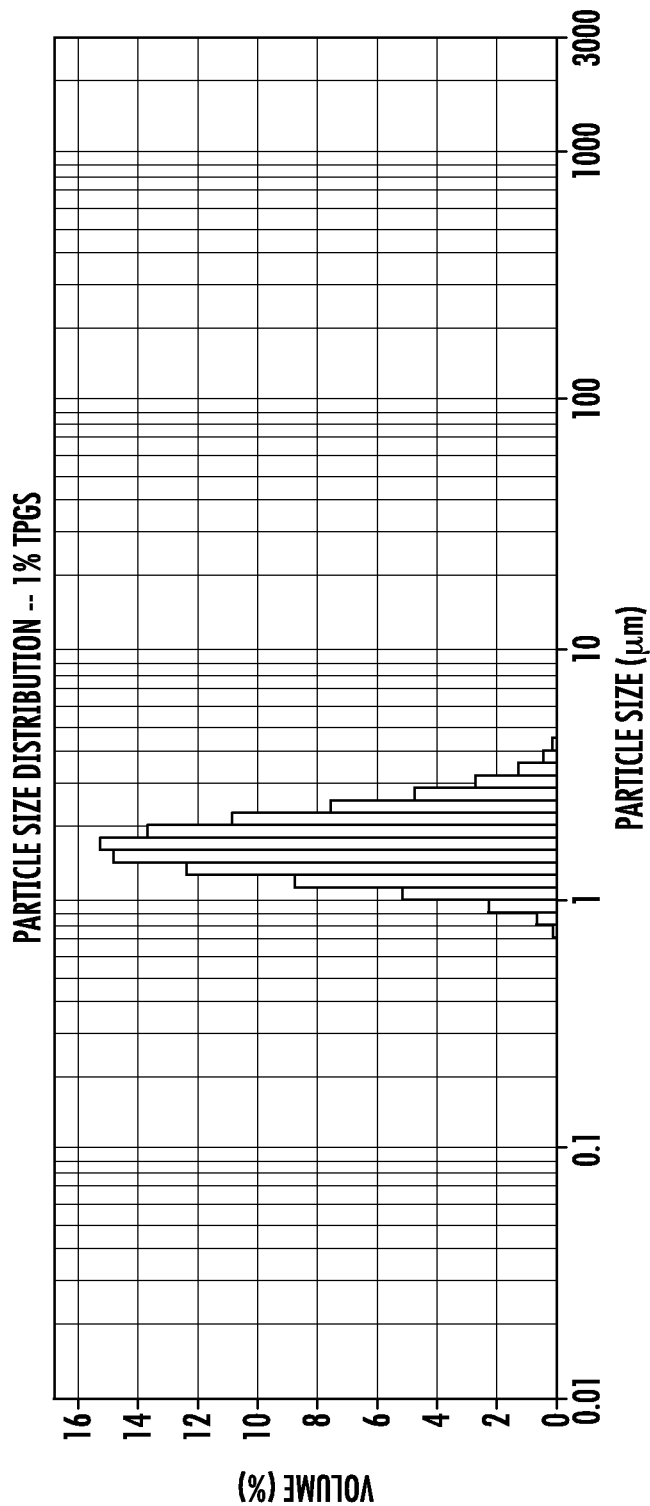
FIG. 3 is graph showing a differential histogram of particle size distribution for a sample in which 3.35% TPGS was used in the premix, in accordance with certain example embodiments. The resultant final product contained 28.88% non-polar component (oil) and 1.0% TPGS. The mean non-polar (oil) component particle size was 1.753 µm for the final product.

After preparation of the 1% TPGS emulsified product, a sample of the product was subjected to particle size analysis as described in Example 1 to determine the size of the non-polar (oil) component droplets within the sample. Initially, the droplets displayed a bi-modal distribution, with peaks around 0.1 µm and 1.7 µm (data not shown). Nevertheless, the 90% of the particles (D(0.90)) were less than 2.116 µm in diameter. When the sample was repeat tested, however, a single peak was observed around 1.7 µm. More particularly, with the repeat test with 1% TPGS in the final emulsification, 90% of the particles (D(0.9)) had a size less than 2.466 µm, while 50% of the particles (D(0.5)) had a size smaller than 1.664 µm. Further, 10% of the particles (D(0.1)) had a particle size smaller than 1.163 µm. The mean particle size (volume weighted mean) was 1.753 µm. A histogram of particle size distribution for the 1% TPGS emulsification (repeat) is shown in FIG. 3.

Example 4—Emulsification with 0.5% TPGS

In this example, an emulsification was prepared as described in Example 1, except that the final emulsification contained 0.5% TPGS. Briefly, the premix was prepared as described in Example 1, with the TPGS comprising 2.13% of the premix and the fish oil comprising the remaining 97.87% of the premix. Following preparation of the emulsification, the final emulsified product included the components shown in Table 5. Further, when 2.13% TPGS was used in the premix, the final emulsion contained 23% fish oil and 0.5% TPGS.

TABLE 5

Components of 0.5% TPGS emulsification

| Component | Percentage |
|---|---|
| Water | 41.7% |
| Grape Color No. 03039 | 0.6% |
| Sorbic Acid | 0.050% |
| Xylitol | 18.000% |
| Citric Acid | 0.400% |
| Glycerin | 8.5% |
| Emulsifier | 3.600% |
| Xanthan Easy | 0.100% |
| Ascorbyl Palmitate | 0.020% |

TABLE 5-continued

Components of 0.5% TPGS emulsification

| Component | Percentage |
|---|---|
| Mixed Berry Flavor | 3.5% |
| Rosemary Extract | 0.03% |
| Premix | 23.5% |
| | (23% fish oil, 0.5% TPGS in final product) |
| TOTAL BATCH | 100.00% |

Figure 4:
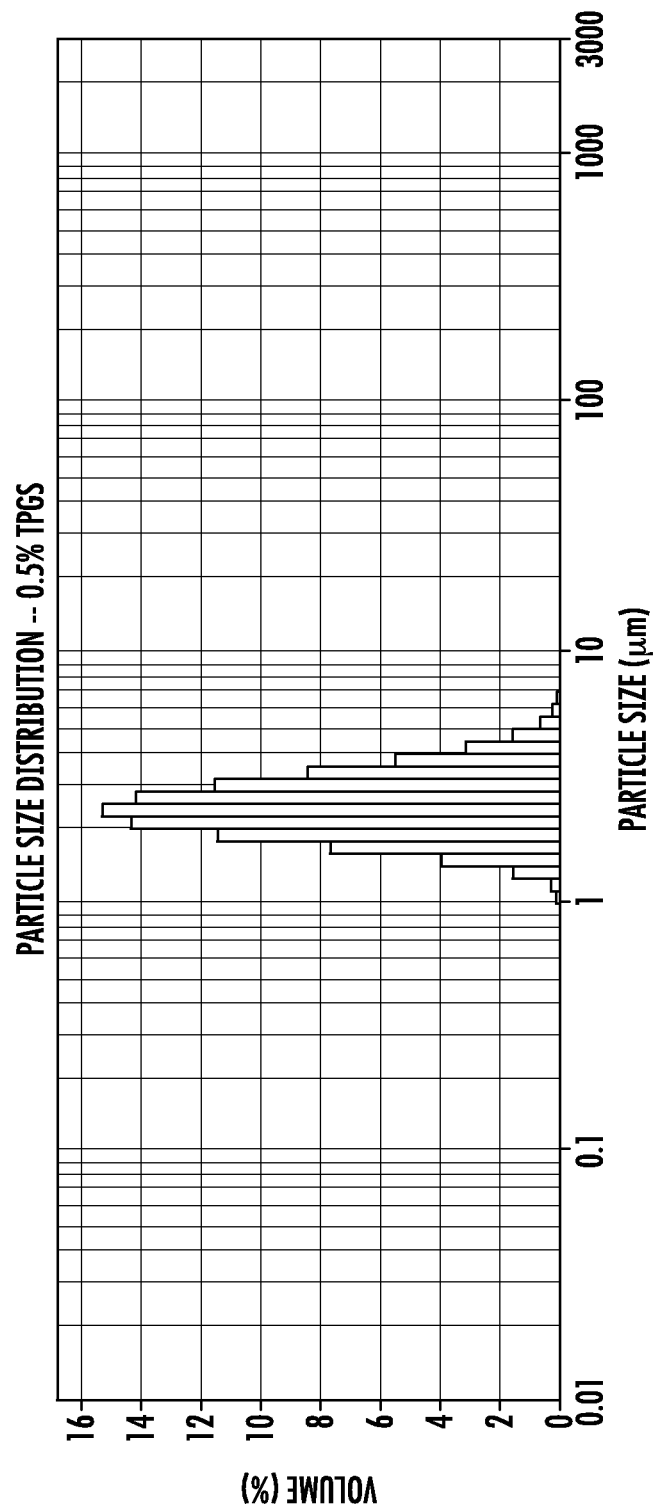
FIG. 4 is graph showing a differential histogram of particle size distribution for a sample in which 2.13% TPGS was used in the premix, in accordance with certain example embodiments. The resultant final product contained 23% non-polar component (oil) and 0.5% TPGS. The mean non-polar (oil) component particle size was 2.570 µm for the final product.

After preparation of the 0.5% TPGS emulsified product, a sample of the product was subjected to particle size analysis as described in Example 1 to determine the size of the non-polar (oil) component droplets within the sample. With 0.5% TPGS in the final emulsification, 90% of the particles (D(0.9)) had a size less than 3.617 µm, while 50% of the particles (D(0.5)) had a size smaller than 2.413 µm. Further, 10% of the particles (D(0.1)) had a particle size smaller than 1.707 µm. The mean particle size (volume weighted mean) was 2.570 µm. A histogram of particle size distribution for the 0.5% TPGS emulsification sample is shown in FIG. 4.

Example 5—Emulsification with 0.3% TPGS

In this example, an emulsification was prepared as described in Example 1, except that the final emulsification contained 0.3% TPGS. Briefly, the premix was prepared as described in Example 1, with the TPGS comprising 1.35% of the premix and the fish oil comprising the remaining 98.65% of the premix. Following preparation of the emulsification, the final emulsified product included the components shown in Table 6. Further, when 1.35% TPGS was used in the premix, the final emulsion contained 22.8% fish oil and 0.3% TPGS.

TABLE 6

Components of 0.3% TPGS emulsification

| Component | Percentage |
|---|---|
| Water | 36.700% |
| Grape Color No. 03039 | 0.600% |
| Sorbic Acid | 0.050% |
| Xylitol | 19.000% |
| Citric Acid | 0.400% |
| Glycerin | 12.000% |
| Emulsifier | 4.500% |
| Xanthan Easy | 0.100% |
| Ascorbyl Palmitate | 0.020% |
| Flavor Passion-Pineapple | 3.500% |
| Rosemary Extract | 0.030% |
| Premix | 23.100% |
| | (fish oil 22.8%, TPGS 0.3% in final product) |
| TOTAL BATCH | 100.000% |

Figure 5:
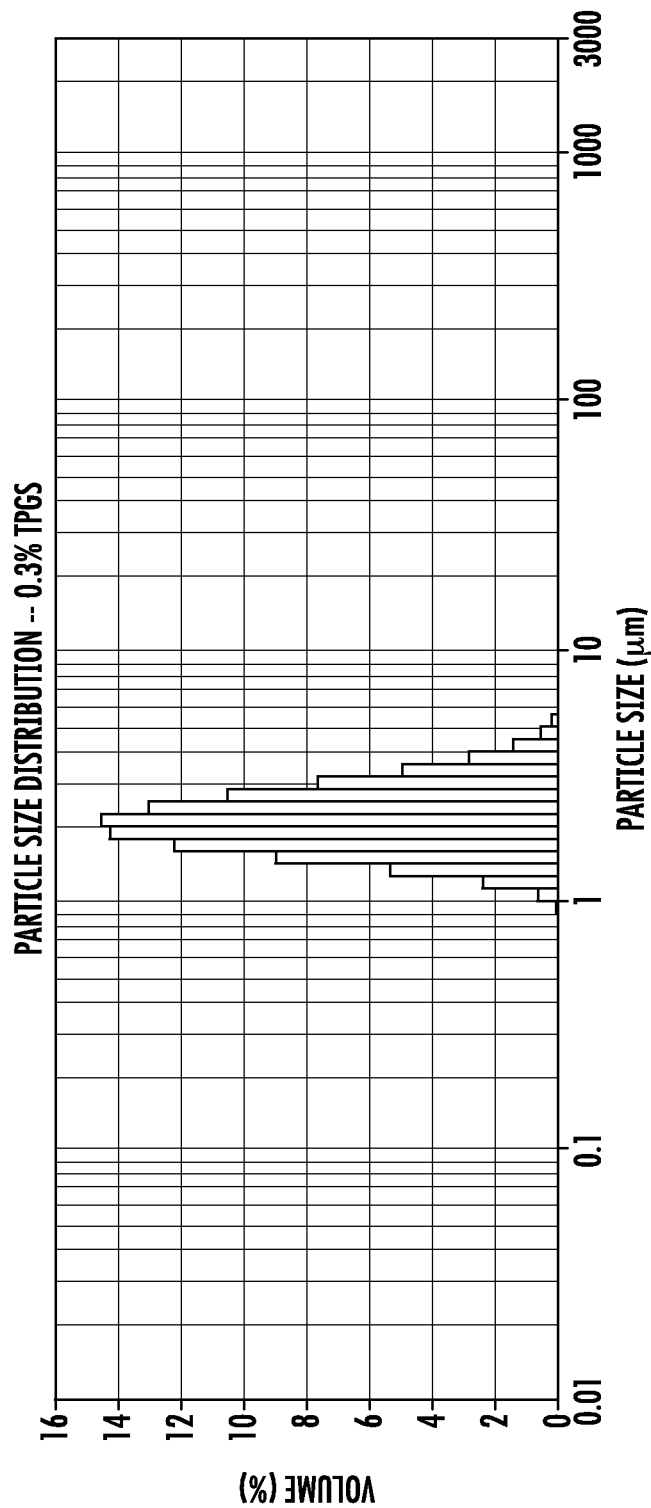
FIG. 5 is graph showing a differential histogram of particle size distribution for a sample in which 1.35% TPGS was used in the premix, in accordance with certain example embodiments. The resultant final product contained 22.8% non-polar component (oil) and 0.3% TPGS. The mean non-polar (oil) component particle size was 2.226 µm for the final product.

After preparation of the 0.3% TPGS emulsified product, a sample of the product was subjected to particle size analysis as described in Example 1 to determine the size of the non-polar (oil) component droplets within the sample. With 0.3% TPGS in the final emulsification, 90% of the particles (D(0.9)) had a size less than 3.177 µm, while 50% of the particles (D(0.5)) had a size smaller than 2.096 µm. Further, 10% of the particles (D(0.1)) had a particle size smaller than 1.449 µm. The mean particle size (volume weighted mean) was 2.226 µm. A histogram of particle size distribution for the 0.3% TPGS emulsification sample is shown in FIG. 5.

Example 6—Sample without TPGS

As a comparison to Examples 1-5, in which TPGS was used in the premix, this example examined particle size of the non-polar (oil) component droplets in the absence of TPGS in the premix. Briefly, a mixture was prepared as described in Example 1, expect that no TPGS was added to the premix. That is, the "premix" component included only fish oil. Following the emulsification steps of Example 1, the final mixture included the components shown in Table 7.

TABLE 7

Fish oil product without TPGS

| Component | Percentage |
|---|---|
| Water | 26.290% |
| Grape Color No. 03039 | 0.600% |
| Sorbic Acid | 0.050% |
| Xylitol | 18.000% |
| Citric Acid | 0.400% |
| Glycerin | 8.5000% |
| Emulsifier | 3.600% |
| Xanthan Easy | 0.100% |
| Ascorbyl Palmitate | 0.020% |
| Flavor Passion-Pineapple | 3.500% |
| Rosemary Extract | 0.030% |
| Mixed tocopherol | 0.910% |
| Premix (fish oil alone) | 38.000% |
| TOTAL BATCH | 100.00% |

Figure 6:
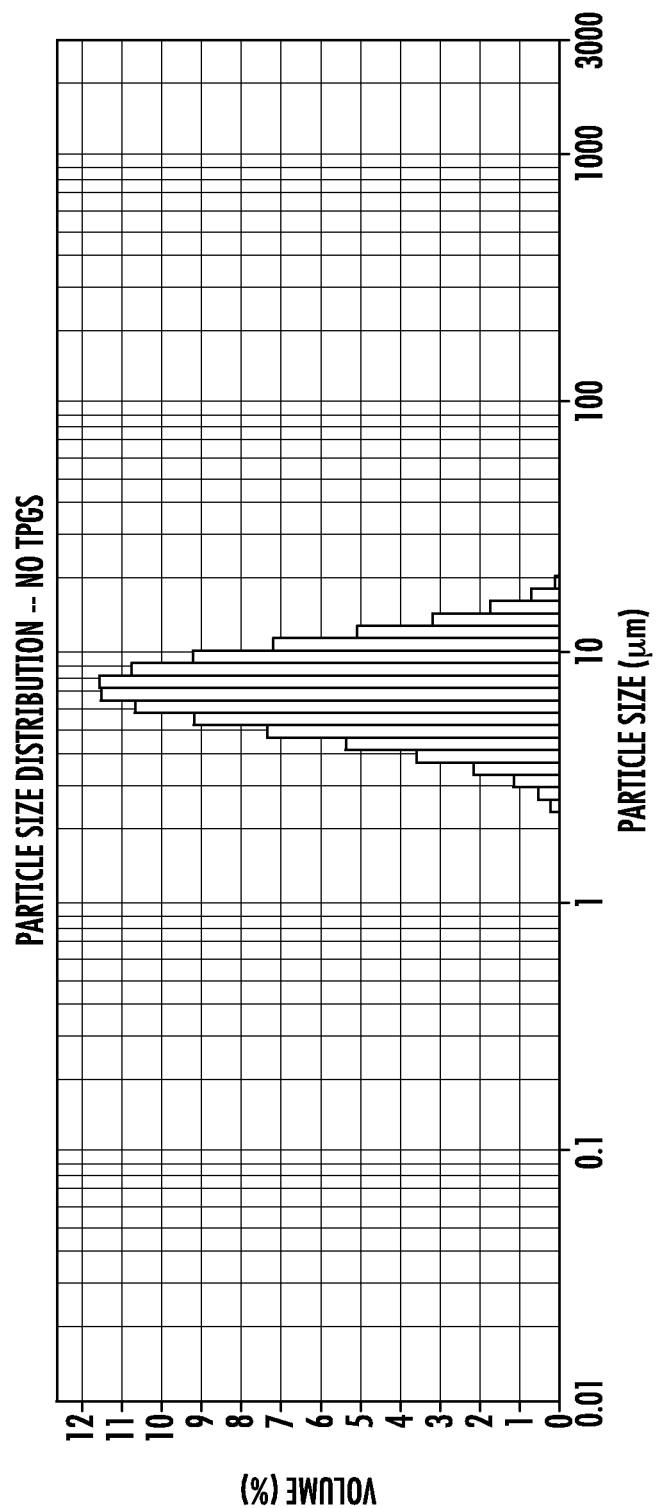
FIG. 6 is graph showing a differential histogram of particle size distribution for a sample in which TPGS was not included in the premix, in accordance with certain example embodiments. The resultant final product contained 38% non-polar component (oil). As shown, however, the mean non-polar (oil) component particle size was 7.470 µm for the final product.

After preparation of the mixture without TPGS, a sample of the mixture was subjected to particle size analysis as described in Example 1 to determine the size of the non-polar (oil) component droplets within the sample. In the absence of TPGS, 90% of the particles (D(0.9)) had a particle size less than 11.349 µm, while 50% of the particles (D(0.5)) had a size smaller than 7.017 µm. Only less than 10% of the particles (D(0.1)) had a particle size smaller than 4.241 µm. The mean particle size (volume weighted mean) was 7.470 µm. A histogram of particle size distribution for the sample without TPGS is shown in FIG. 6. Compared to Examples 1-5, which included TPGS in the premix, the absence of TPGS in the premix resulted in a substantially larger mean and median particle size of the non-polar (oil) component droplets.

Discussion

Based on these data, the use of TPGS with the methods and systems as described can substantially reduce the particle size of oil droplets within the emulsion. Likewise, a higher percentage of TPGS was generally correlated with a smaller particle size (the exception being 0.3 TPGS). Nonetheless, as compared with no TPGS, use of TPGS according to the methods and systems described herein resulted in substantially reducing the particle size of the oil particles. For example, the mean particle size with 5% TPGS in the final product sample was 0.713 µm. In sharp contrast, the mean particle size without TPGS in the premix was 7.470 µm. Hence, use of 5% TPGS for the final emulsion product, in accordance with the methods and systems described herein, resulted in greater than a 10-fold decrease in particle size of the lipid (oil) component in the emulsion.

In view of the many possible embodiments to which the principles of the disclosed invention may be applied, it should be recognized that the illustrated example embodiments are only preferred examples of the invention and should not be taken as limiting the scope of the invention. Rather, the scope of the invention is defined by the following claims. We therefore claim as our invention all that comes within the scope and spirit of these claims.

I claim:

1. A process for forming an oil-in-water emulsion, comprising combining under high-shear mixing:
   a) an oil phase comprising:
      i) d-α-tocopheryl polyethylene glycol succinate ("TPGS") or one or more derivatives thereof, and
      ii) one or more non-polar compounds; and
   b) an aqueous phase comprising:
      i) less than about 15% by weight of one or more emulsifiers, and
      ii) the balance water and optionally one or more carriers;
   wherein the emulsion comprises less than 2% by weight TPGS or derivatives thereof and about 20% to about 35% by weight of the one or more non-polar compounds and wherein the oil phase droplets have a median particle size greater than 1 µm but less than or equal to 3 µm.

2. The process of claim 1, wherein the emulsion comprises less than 1% by weight TPGS or derivatives thereof.

3. The process of claim 1, wherein the aqueous phase comprises less than about 5% by weight of the emulsifier.

4. The process of claim 1, wherein the non-polar compound comprises an omega-3 fatty acid, omega-5 fatty acid, omega-6 fatty acid, omega-7 fatty acid, or mixture thereof.

5. The process of claim 1, wherein the aqueous phase further comprises gum arabic, xanthan gum, guar gum, or a combination thereof.

6. The process of claim 1, wherein the aqueous phase further comprises an organic acid.

7. The process of claim 6, wherein the organic acid is citric acid, ascorbic acid, malic acid, or a combination thereof.

8. The process of claim 1, wherein the aqueous phase further comprises from about 1% to about 20% by weight glycerin.

9. The process of claim 1, wherein the aqueous phase further comprises xylitol, erythritol, or a combination thereof.

10. The process of claim 1, wherein the oil phase further comprises from about 1% to about 5% by weight tocopherol, rosemary extract, or a combination thereof.

11. The process claim 1, wherein the oil phase and the aqueous phase further comprise a preservative.

12. The process of claim 11, wherein the oil phase preservative is sorbic acid.

13. The process of claim 11, wherein the aqueous phase preservative is potassium sorbate, sodium benzoate, or combination thereof.

14. A method for providing an emulsion, comprising:
   providing a first mixture comprising d-α-tocopheryl polyethylene glycol succinate ("TPGS") or derivative thereof and a non-polar compound or mixture of non-polar compounds, wherein the TPGS or derivative thereof is present in an amount less than 10% by weight of the first mixture and the non-polar compound or mixture of non-polar compounds are present in amount at least 90% by weight of the first mixture;
   providing a second mixture, wherein the second mixture comprises water and one or more emulsifiers and wherein the one or more emulsifiers comprise less than about 15% of the second mixture;

combining the first mixture with the second mixture under high-shear to form an emulsion of the non-polar compound or mixture of non-polar compounds, wherein the non-polar compounds or mixture thereof are present in the emulsion in droplets having a median particle size greater than 1 μm but less than or equal to about 3 μm, wherein the non-polar compounds or mixture thereof comprise about 20% to about 35% by weight of the emulsion, and wherein the TPGS or derivative thereof does not exceed 2% by weight of the emulsion.

15. The method of claim 14, wherein the TPGS or derivative thereof does not exceed 1% by weight of the emulsion.

16. The method of claim 14 wherein the non-polar compound or mixture thereof comprises an omega-3 fatty acid, an omega-5 fatty acid, an omega-6 fatty acid, an omega-7 fatty acid, or mixture thereof.

17. The method of claim 14, wherein the emulsifier comprises gum arabic, xanthan gum, guar gum, or a combination thereof.

18. The method of claim 14, wherein the emulsion comprises less than 5% of the emulsifier.

19. The method of claim 14, wherein the non-polar compounds or mixture thereof are present in the emulsion in droplets having a median particle size of about 2 μm.

20. An oil-in-water emulsion, comprising water and:
a) an emulsifier;
b) d-α-tocopheryl polyethylene glycol succinate ("TPGS") or a derivative thereof; and
c) about 20% to about 35% by weight of one or more lipids;

wherein the emulsifier is present in an amount less than 10% by weight of the emulsion, wherein the TPGS is present in an amount less than 2% by weight of the emulsion, and wherein the lipids are present in the emulsion as droplets having a median particle size of greater than 1 μm but less than or equal to about 3 μm.

21. The emulsion of claim 20, wherein the droplets have a median particle size of about 2 μm.

22. The emulsion of claim 20, wherein the one or more lipids is an omega-3 fatty acid, omega-5 fatty acid, omega-6 fatty acid, omega-7 fatty acid, or mixture thereof.

23. The emulsion of claim 20, wherein the emulsion comprises about 23% by weight of the one or more lipids.

24. The emulsion of claim 20, wherein the TPGS comprises less than 1% of the emulsion.

25. The emulsion of claim 20, wherein the TPGS comprises less than 0.5% of the emulsion.

* * * * *